United States Patent [19]

Hoogland et al.

[11] Patent Number: 5,279,968

[45] Date of Patent: Jan. 18, 1994

[54] METHOD OF LABELLING LEUCOCYTES WITH TC-99M, D,1-HMPAO

[75] Inventors: Dennis Hoogland, Simi Valley, Calif.; Deborah Kaminsky, Buffalo Grove, Ill.

[73] Assignee: Syncor International Corporation, Chatsworth, Calif.

[21] Appl. No.: 383,366

[22] Filed: Jul. 20, 1989

[51] Int. Cl.$^5$ .............. G01N 23/00; G01N 1/18; C09K 11/00

[52] U.S. Cl. .............. 436/57; 436/177; 435/7.24; 252/645

[58] Field of Search .......... 436/57, 501, 503, 504, 436/547, 548, 804, 177; 435/7, 7.24; 424/1.1; 534/10, 14; 252/644, 645, 646

[56] References Cited

U.S. PATENT DOCUMENTS

| | | | |
|---|---|---|---|
| 3,725,295 | 4/1973 | Eckelman et al. | 252/645 |
| 4,311,688 | 1/1982 | Burchiel et al. | 422/61 |
| 4,434,237 | 2/1984 | Dinarello | 436/804 |
| 4,443,426 | 4/1984 | Thakur | 534/10 |
| 4,452,774 | 6/1984 | Jones et al. | 534/14 |
| 4,455,379 | 6/1984 | Bekesi et al. | 436/504 |
| 4,456,690 | 6/1984 | Cais et al. | 436/804 |
| 4,666,834 | 5/1987 | Bekesi et al. | 436/804 |

OTHER PUBLICATIONS

H. J. Danpure et al., Nuclear Medicine Communications, (1988) vol. 9, pp. 681–685.

A. M. Peters et al., Lancet (1986) vol. 2 pp. 946–949.

Joseph C. Hung et al., Journal of Nuclear Medicine (1988) vol. 29, pp. 1568–1576.

N. N. Solanki et al., Nuclear Medicine Communications (1988) vol. 9, pp. 753–761.

Operating Instructions for the Hema-Tek Aliquot Mixer from Miles Laboratories, Inc.

Appendex "A": Statement regarding a public use of a Rocker Arm.

Primary Examiner—Lyle A. Alexander
Assistant Examiner—N. Bhat

[57] ABSTRACT

An improved method for radio-labelling leucocytes in vitro with Tc-99m d,1-HMPAO (Technetium-99m-d,1-hexamethyl propyleneamine oxime) for use in scintigraphic imaging of inflammatory lesions enhances the labelling efficiency by incubating the leucocytes with Tc-99m d,1-HMPAO in the presence of an acid citrate dextrose solution and by depleting residual RBCs from the leucocytes prior to such incubation step. The RBC depletion is accomplished by means of a rocking step.

3 Claims, No Drawings

METHOD OF LABELLING LEUCOCYTES WITH TC-99M, D,1-HMPAO

The invention relates to methods for radiolabelling leucocytes in vitro with gamma-emitting radionuclides. The radiolabelled leucocytes are employed for imaging inflammatory lesions by scintigraphy after injection into a patient. More particularly, the invention relates to methods for enhancing the labelling efficiency of Tc-99m d,1-HMPAO (Technetium-99m-d,1-hexamethylpropyleneamine oxime) with respect to the labelling of leucocytes in vitro while maintaining sterility and viability.

BACKGROUND

Methods for radiolabelling human leucocytes with gamma emitters have been reviewed by H. J. Danpure and S. Osman ("A Review of Methods of Separation and Radiolabelling Human Leucocytes," Nuclear Medicine Communications (1988); vol. 9, 681–685). Danpure and Osman indicate that successful radiolabelling methods employ neutral lipophilic agents which chelate the selected gamma emitting radionuclide and carry the radionuclide across the cellular membrane into the patient's or donor's isolated leucocytes. Once inside the leucocyte, the lipophilic chelator may be degraded or otherwise modified so as to produce a hydrophilic radionuclide product. The hydrophilic radionuclide product remains entrapped within the leucocytes for a period sufficiently long to allow rapid injection of the labelled leucocytes into the patient, migration of the labelled leucocytes to inflamation sites, and scintigraphic imaging of inflamation sites by means of the labelled leucocytes. Danpure and Osman indicate that the gamma-emitting radionuclide Indium-111 oxine has been successfully employed in clinical settings for radiolabelling mixed leucocytes for scintigraphic imaging.

As an alternative to Indium-111 oxine, A. M. Peters et al. introduced Tc-99m d,1-HMPAO (Technetium-99m-d,1-hexamethylpropylene-amine oxime) for radiolabelling leucocytes ("Preliminary Clinical Experience with Tc-99m d,1-HMPAO for Labelling Leucocytes and Imaging Infection," Lancet (1986); vol. 11, 945–949) Technetium-99m is a widely available generator-produced radionuclide ideally suited for gamma detection. Use of Tc-99m d,1-HMPAO can produce a good scintigraphic image at a relatively low radiation dosage. The conversion of Tc-99m d,1-HMPAO from a lipophilic form to a hydrophilic form has been characterized by Joseph C. Hung et al. ("Kinetic Analysis of Technetium-99m d,1-HM-PAO Decomposition in Aqueous Media," Journal of Nuclear Medicine (1988); vol. 29, 1568–1576).

An advanced method for labelling leucocytes with Technetium-99m d,1-HM-PAO has been disclosed by N. N. Solanki et al. ("A Rapid Method for the Preparation of TC99-m Hexametazine-Labelled Leucocytes," Nuclear Medicine Communications (1988); vol. 9, 753–761). Solanki et al. indicate that leucocytes are best separated from whole blood by a $1 \times g$ sedimentation followed by a gentle ($100 \times g$) centrifugation of the resultant leucocyte platelet-rich plasma (LPRP). The resultant pellet is then re-suspended in 10% cell free plasma (CFP) and incubated with Tc-99m d,1-HMPAO. Solanki et al. claim a labelling efficiency of 25.9% when employing the recommended reconstitution volume and a labelling efficiency of 49% when employing a low reconstitution volume.

Achieving a labelling efficiency in excess of 25.9% with Tc-99m d,1-HMPAO while employing the recommended reconstitution volume is desirable since enhanced labelling efficiency reduces the size of the blood sample which must be drawn from the patient, enhances the resultant image quality, and decreases the amount of Technetium-99m d,1-HM-PAO reagent which must be employed, and minimizes contamination by red blood cells (RBCs).

SUMMARY

The efficiency of labelling leucocytes with Tc-99m d,1-HMPAO may be significantly enhanced by carefully controlling the incubation conditions of the labelling step. In particular, the depletion of residual red blood cells (RBCs) from the leucocytes prior to the labelling step significantly enhances the labelling efficiency. Also, the presence of Acid Citrate Dextrose solution (ACD) added to the leucocytes during the labelling step further enhances labelling efficiency. A combination of RBC depletion and ACD addition increases the labelling efficiency of leucocytes with respect to Tc-99m d,1-HMPAO to a level of 80-95%, using Solanki's recommended reconstitution volume.

DETAILED DESCRIPTION OF THE INVENTION

A preferred protocol for high efficiency labelling of leucocytes with Tc-99m d,1-HMPAO is provided as follows:

1. A blood sample is drawn from the patient using a 60 milliliter syringe. Prior to drawing the blood sample, an aliquot of ACD solution should be drawn into the syringe. ACD solution serves as an anticoagulant and conventionally has a composition which includes 25 grams of sodium citrate, 8.75 grams of citric acid, and 6 grams dextrose per liter of sterile water for injection. After the blood is drawn into the syringe the ratio of blood volume to anticoagulant should not exceed 5:1. For example, 42 milliliters of blood may be drawn into a 60 milliliter syringe which has been preloaded with 8 milliliters of ACD solution.

2. The syringe is then positioned with its needle pointed vertically upward so as to allow the blood to sediment ($1 \times g$) for 30–45 minutes. During sedimentation, the RBCs settle to the bottom of the syringe toward the plunger while leucocyte rich plasma remains at the top of the syringe proximate to the needle. In an alternative embodiment, sedimentation of the RBCs may be accelerated by the addition of Hespan (TM) (6% hetastarch in 0.9% sodium chloride, DuPont, Del.).

3. The leucocyte rich plasma is then expressed from the syringe into a first centrifuge tube, preferably a conventional 50 milliliter disposable centrifuge tube having a conical bottom and a composition of polypropylene. The leucocyte rich plasma is then centrifuged at $450 \times g$ for 7 minutes in order to pellet the leucocytes while forming a supernatant of platlet rich plasma (PRP).

4. The PRP supernatant is then withdrawn from the first centrifuge tube and transferred to a second centrifuge tube. The second centrifuge tube is then centrifuged at $950 \times g$ for 10 minutes to form platlet poor plasma (PPP). The PPP is then saved for use in steps 12 and 13 below.

5. In the meantime, the leucocyte pellet from the first centrifuge tube is resuspended in 4 milliliters of isotonic saline, i.e. 0.9% sodium chloride in sterile water for injection. Care should be taken when resuspending the leucocyte pellet not to swirl too vigorously so as to cause the formation of foam.

6. The first centrifuge tube containing the resuspended leucocytes is then mounted onto a rocker arm for separating residual RBCs from the leucocytes. The preferred rocker arm may be constructed by modifying a "Hema Tek" (TM) Aliquot Mixer, Model 4651, manufactured by the Ames Division of Miles Laboratories, Inc. (Elkhart, Ind.). The unmodified "Hema Tek" (TM) Aliquot Mixer consists of a tilting table, an actuating motor and a base. The platform tilts back and forth at 12 or 18 cycles per minute for mixing specimen samples. Other similar rocking devices may be obtained from Clay Adams (Nutator Mixer model #1105) and from American Scientific Products (American (TM) Tube Rocker catalog #R4185-10). Prior to modification, the tilting table cradles the specimen tubes in a horizontal position. In the preferred mode for constructing the rocker arm, the tilting table of the "Hema Tek" (TM) Aliquot Mixer is modified so as to securely brace one or more centrifuge tubes in a vertical position. When the rocker arm is activated, the centrifuge tubes oscillate around this vertical position. The motion of a single vertical centrifuge tube mounted upon the rocker arm is similar to that of a metronome which oscillates at 18 cycles per minute. The leucocyte suspension is allowed to rock upon the rocker arm for 15 minutes. During this rocking step, the leucocytes settle to the bottom of the centrifuge tube while the residual RBCs remain in the supernatant. The exact biochemical mechanism for this separation is unknown. It is speculated that the RBCs undergo a flocculation reaction or are otherwise hindered from settling with the leucocytes due to a surface charge phenomenon.

7. After rocking for 15 minutes, the rocker arm is stopped. The leucocytes are then depleted of residual RBCs by carefully removing and discarding the top 1 or 2 milliliters of supernatant. The volume of supernatant which is removed is then replaced with an equal volume of isotonic saline and the leucocytes are resuspended.

8. The resuspended leucocytes are then rocked for 10 more minutes to separate out further residual RBCs. After 10 minutes, the rocker arm is again stopped. Again the rocking step has caused the leucocytes to settle to the bottom and the residual RBCs to remain within the supernatant. After the rocker arm has been stopped, the leucocytes are then further depleted of residual RBCs by carefully removing the top 1 or 2 milliliters of supernatant.

9. Then 2 milliliters of a 10% diluent of the ACD solution is added to the leucocyte suspension. The presence of ACD during the Tc-99m d,1-HMPAO incubation (step 11) enhances the efficiency of labelling. The concentration of the ACD in the leucocyte suspension should not exceed a volume to volume ratio of 1:10 as exposure to excess ACD may detract from the subsequent viability of the leucocytes.

10. In the meanwhile, Tc-99m d,1-HMPAO may be prepared from a Ceretec (TM) kit supplied by Amersham International plc. (Amersham, Buckinghamshire, England). The kit includes 0.5 micrograms of d,1-4, 8-diaza-3,6,6,9,-tetramethyl-undecane-2,10-dione bioxime (d,1-HMPAO), 7.6 micrograms stannous chloride dihydrate, and 4.5 milligrams sodium chloride, freeze-dried and stoppered under nitorgen. Technetium pertechnetate may be obtained from a commercial Mo-99m/Tc-99m generator. Tc-99m d,1-HMPAO is prepared using 30 millicuries (1110 MBq) of sodium [Tc-99m]pertechnetate drawn into a vial containing 2 milliliters of isotonic saline. Only eluate obtained less than 2 hours from a generator eluted within a 24 hour period should be used or per package insert instructions. Ceretec (d,1-HMPAO) is then tagged by chelation to [Tc-99m]pertechnetate as specified by the manufacturer to form Tc-99m d,1-HMPAO. As a quality control for this chelation reaction, the yield of lipophilic product, i.e. Tc-99m d,1-HMPAO, may be determined by appropriate chromatographic systems or procedures using an appropriate solvent.

11. The leucocytes of step 9 are then labelled by the addition of Tc-99m d,1-HMPAO. The mixture is incubated for 15 minutes and swirled every 5 minutes. The addition of ACD to the leucocytes in step 9 enhances the efficiency of this reaction. The efficiency of the reaction is further enhanced by the depletion of residual RBCs in steps 5-8. The precise biochemical mechanism for this enhancement is unknown. However, it is thought that RBCs and platelets contain reducing agents which prematurely degrade the Tc-99m d,1-HMPAO. Also, the suspension of the leucocytes in step 9 enhances the efficiency of the labelling reaction by increasing the access of the leucocytes with respect to the labelling reagents. For patients with normal and elevated white cell counts, the labelling efficiency of this improved labelling method may rise within the range of 80-95%.

12. After the 15 minute incubation, 1 milliliter of platelet poor plasma (PPP) is added to the labelled leucocytes as part of a wash step. The leucocytes and PPP are mixed by swirling. The leucocytes are then separated from unreacted Tc-99m d,1-HMPAO by centrifugation at 450×g for 7 minutes. The supernatant is then removed and discarded.

13. The washed pellet of labelled leucocytes is then resuspendend in platelet poor plasma (PPP) or saline solution (0.9% sodium chloride) to which 10% ACD solution may be added. The resuspended leucocytes should be injected into the patient as soon as possible, i.e. within 1 hour or not to exceed approximately 5 hours from time of the original blood collection.

The invention revolves around the preparation of the leucocyte sample for labelling with the Tc-99m d,1-HMPAO, i.e. the depletion of residual RBCs from the leucocytes (steps 5-8) prior to the labelling step and the addition of ACD (step 9). It is the addition of these steps which enables the labelling step to achieve a significant enhancement of the labelling efficiency. The above protocol is merely exemplary of a preferred mode for practicing these aspects of the invention. For example, the protocol may be modified with good results by eliminating the second rocking step, i.e. step 8, and deleting the addition of isotonic saline in step 7.

EXAMPLE

Comparative tests were performed for determining the relative enhancement of tagging efficiency with and without the addition of ACD during incubation (Step 9) and with and without the rocker steps for depleting RBCs from the leucocytes prior to incubation (steps 5-8), i.e. ACD (step 9):: saline (step 9 eliminated):rocker (steps 5-8)::no rocker (steps 5-8 eliminated). The measured tagging efficiency of samples which had not been depleted of RBCs prior to incubation (steps 5-8) were determined both with and without a subsequent RBC depletion step. Samples from which RBCs had not been depleted included a significant contaminant of tagged RBCs. (This is a measure of the RBC contaminant characteristic of prior art methods.) Samples from which RBCs had been depleted were substantially without any contaminant of tagged RBCs. Tagging efficiency is a measure of label incorporation and was calculated by the method of Solanki et al. (supra). The tests were performed with blood taken from a healthy human volunteer having a relatively low white cell count. Accordingly, the overall tagging efficiencies were lower than normal. The labelling protocol followed the example provided above with the addition or deletion of steps 5-8 and step 9 and with the addition of the hetastarch option in step 2. The test results are provided as follows:

| Conditions | Tagging Efficiency w/o RBC Depletion | RBC Contamination | Tagging Efficiency with RBC Depletion |
| --- | --- | --- | --- |
| 1. ACD & Rocker | | | 56% |
| 2. ACD & no Rocker | 69% | 18% | 51% |
| 3. Saline & Rocker | | | 43% |
| 4. Saline & no Rocker | 54% | 23% | 31% |

What is claimed is:

1. An improved method for radio-labeling leucocytes with Tc-99m d,1-HMPAO including the following steps:
   Step A: separating the leucocytes from whole blood; and then
   Step B: labeling the separated leucocytes with Tc-99m d,1-HMPAO;
   wherein the improvement comprises the following further step:
   Step A(2): after said Step A and prior to said Step B, depleting residual RBCs from the leucocytes by resuspending the leucocytes in an isotonic saline solution, rocking the resuspended leucocytes for preferentially settling out the leucocytes, and then removing residual RBCs which remain within the supernatant.

2. An improved method for radio-labeling leucocytes as described in claim 1 wherein the improvement comprises the following further step:
   step A(3): after said Step A(2) and prior to said Step B, further depleting residual RBCs from the leucocytes by again resuspending the settled leucocytes in isotonic saline, rocking the resuspended leucocytes for causing the leucocytes to preferentially settle out, and then removing residual RBCs which remain within the supernatant.

3. An improved method for radio-labeling leucocytes with Tc99m d,1-HMPAO including the following steps;
   Step A: separating the leucocytes from whole blood; and then
   Step B: labeling the separated leucocytes with Tc-99m d,1-HMPAO;
   wherein the improvement comprises the following further steps:
   Step A(1): after said Step A and prior to said Step B, depleting residual RBCs from the leucocytes by resuspending the leucocytes in an isotonic saline solution, rocking the resuspended leucocytes for preferentially settling out to leucocytes, and then removing residual RBDs which remain within the supernatant; and then
   Step A(2): after said Step A(1) and prior to said Step B, adding an ACD solution to the leucocytes for enhancing the labelling efficiency.

* * * * *